(12) United States Patent
Clemensen et al.

(10) Patent No.: US 12,290,350 B2
(45) Date of Patent: May 6, 2025

(54) OXYGEN CONSUMPTION AND ENERGY EXPENDITURE MONITORING

(71) Applicants: Children's Medical Center Corporation, Boston, MA (US); COSMED S.r.l., Rome (IT)

(72) Inventors: Peter Clemensen, Odense (DK); John Kheir, Charlestown, MA (US); Brian Polizzotti, Swampscott, MA (US); Arne Bo Thomsen, Tommerup (DK)

(73) Assignees: Children's Medical Center Corporation, Boston, MA (US); COSMED S.r.l., Rome (IT)

( * ) Notice: Subject to any disclaimer, the term of this patent is extended or adjusted under 35 U.S.C. 154(b) by 1225 days.

(21) Appl. No.: 16/762,456

(22) PCT Filed: Nov. 9, 2018

(86) PCT No.: PCT/US2018/059961
§ 371 (c)(1),
(2) Date: May 7, 2020

(87) PCT Pub. No.: WO2019/094680
PCT Pub. Date: May 16, 2019

(65) Prior Publication Data
US 2020/0359935 A1 Nov. 19, 2020

Related U.S. Application Data

(60) Provisional application No. 62/583,927, filed on Nov. 9, 2017.

(51) Int. Cl.
*A61B 5/083* (2006.01)
*A61B 5/00* (2006.01)
(Continued)

(52) U.S. Cl.
CPC .......... *A61B 5/0833* (2013.01); *A61B 5/0816* (2013.01); *A61B 5/0836* (2013.01);
(Continued)

(58) Field of Classification Search
CPC ... A61B 5/0833; A61B 5/0816; A61B 5/0836; A61B 5/087; A61B 5/097; A61B 5/4836;
(Continued)

(56) References Cited

U.S. PATENT DOCUMENTS 4,233,842 A * 11/1980 Raemer ...................... G01F 1/74
73/861.04
5,069,220 A * 12/1991 Casparie ................ A61B 5/087
73/23.3

(Continued)

OTHER PUBLICATIONS

PCT International Preliminary Report on Patentability in International Appln. No. PCT/US2018/059961, dated May 22, 2020, 10 pages.

(Continued)

*Primary Examiner* — Rene T Towa
*Assistant Examiner* — Justin Xu
(74) *Attorney, Agent, or Firm* — Fish & Richardson P.C.

(57) ABSTRACT

A patient ventilation system and a computing device-implemented method determine oxygen consumption in a mechanically ventilated subject includes receiving a signal representing a total flow at an inspiratory outlet of a ventilator, calculating a transport delay time between inspiratory and expiratory gas sample points in a patient ventilation circuitry, transmitting a signal to an inlet selector valve to selectively open a fluid path between the inspiratory gas sample point and an oxygen sensor or between the expiratory gas sample point and the oxygen sensor, receiving data representing oxygen content and carbon dioxide content over a period of time, calculating oxygen consumption data over the period of time from the data representing the total (Continued)

flow, oxygen content and carbon dioxide content and from the transport delay time, and displaying the oxygen consumption data over the period of time.

19 Claims, 9 Drawing Sheets

(51) Int. Cl.
| | |
|---|---|
| A61B 5/08 | (2006.01) |
| A61B 5/087 | (2006.01) |
| A61B 5/097 | (2006.01) |
| A61M 16/00 | (2006.01) |
| A61M 16/08 | (2006.01) |
| A61M 16/10 | (2006.01) |
| A61M 16/12 | (2006.01) |
| A61M 16/16 | (2006.01) |
| A61M 16/20 | (2006.01) |
| G09B 23/28 | (2006.01) |
| G09B 23/30 | (2006.01) |

(52) U.S. Cl.
CPC .............. *A61B 5/087* (2013.01); *A61B 5/097* (2013.01); *A61B 5/4836* (2013.01); *A61B 5/742* (2013.01); *A61M 16/024* (2017.08); *A61M 16/0833* (2014.02); *A61M 16/085* (2014.02); *A61M 16/202* (2014.02); *A61B 2503/045* (2013.01); *A61M 2016/003* (2013.01); *A61M 2016/1025* (2013.01); *A61M 16/1055* (2013.01); *A61M 16/16* (2013.01); *A61M 2202/0208* (2013.01); *A61M 2205/3306* (2013.01); *A61M 2205/52* (2013.01); *A61M 2230/432* (2013.01); *A61M 2240/00* (2013.01); *G09B 23/303* (2013.01)

(58) Field of Classification Search
CPC .............. A61B 5/742; A61B 2503/045; A61B 2503/04; A61B 2503/08; A61M 16/024; A61M 16/0833; A61M 16/085; A61M 16/202; A61M 16/1055; A61M 16/16; A61M 2016/003; A61M 2016/1025; A61M 2202/0208; A61M 2205/3306; A61M 2205/52; A61M 2230/432; A61M 2240/00; A61M 16/125; A61M 2016/103; A61M 2205/7518; A61M 2230/435; G09B 23/303; G09B 23/28

See application file for complete search history.

(56) References Cited

U.S. PATENT DOCUMENTS

| | | | |
|---|---|---|---|
| 5,072,737 A | * | 12/1991 | Goulding ............... A61B 5/097 |
| | | | 128/205.12 |
| 6,439,231 B1 | | 8/2002 | Fukunaga et al. |
| 2002/0120207 A1 | | 8/2002 | Hoffman et al. |
| 2002/0173728 A1 | * | 11/2002 | Mault .................... A61B 5/029 |
| | | | 128/204.22 |
| 2003/0106554 A1 | * | 6/2003 | de Silva ................ A61M 16/12 |
| | | | 128/204.22 |
| 2004/0221845 A1 | | 11/2004 | Pranger et al. |
| 2006/0201503 A1 | * | 9/2006 | Breen ............. A61M 16/0875 |
| | | | 128/204.22 |
| 2007/0123792 A1 | * | 5/2007 | Kline .................... A61B 5/087 |
| | | | 600/323 |
| 2011/0180063 A1 | * | 7/2011 | Hunsicker ............ A61M 16/14 |
| | | | 128/200.14 |
| 2013/0255687 A1 | * | 10/2013 | Rahlf .................. A61M 16/024 |
| | | | 128/204.26 |
| 2017/0325716 A1 | * | 11/2017 | Coleman ............... A61B 5/087 |

OTHER PUBLICATIONS

PCT International Search Report and Written Opinion in International Appln. No. PCT/US2018/059961, dated Jan. 16, 2019, 17 pages.

* cited by examiner

OXYGEN CONSUMPTION AND ENERGY EXPENDITURE MONITORING

CROSS-REFERENCE TO RELATED APPLICATIONS

This application is a 371 U.S. National Phase Application of PCT/US2018/059961, filed on Nov. 9, 2018, which claims the benefit of priority under 35 U.S.C. Section 119(e) to U.S. Provisional Patent Application No. 62/583,927, filed on Nov. 9, 2017, the entire contents of which are incorporated herein by reference.

TECHNICAL FIELD

This invention relates to mechanical ventilation systems and methods for determining oxygen consumption.

BACKGROUND

In the conventional way of measuring oxygen consumption on a Breath-by-Breath (B-b-B) basis, respiratory flow and oxygen concentration are measured with a proximal flowmeter and oxygen analyzer, respectively, during inspiration and expiration of a patient. Flowmeters do not cope well with humidified ventilation systems because water tends to affect the detection mechanism causing calibration to change when measuring for longer durations. Additionally, a short gas analyzer response time and perfect time alignment between flow and gas concentration signals are required to obtain accurate values. However, while flowmeters typically respond instantaneously, gas analyzers respond with a delay (typically 1 second) due to the transport of gas from the sampling site to the gas detector through the gas sample line. Even small errors in time alignment can cause significant errors in the calculated oxygen consumption, with an incorrect time alignment of 20 ms causing an error in the calculated oxygen consumption of up to 20%.

Another method for measuring oxygen consumption is the classical Douglas method where oxygen is measured during inspiration or assumed to be equal to the concentration in air. Expired gas is collected in a bag and the oxygen concentration and the volume of the bag are measured, wherein the expired volume is corrected for temperature and water vapor content. In principle, the oxygen consumed is the difference between oxygen concentrations in the inspired air and in the bag multiplied by the respired volume.

Such prior systems are not well adapted to neonate systems as measurement of oxygen consumption in newborns is challenging for several reasons. For example, bag collection methods are not adapted for the very low flows breathed by neonates. Placing a B-b-B flowmeter in the apparatus dead space between endotracheal tube and Y-piece of the ventilator is critical, but can be difficult for patients with a small breathing volume such as newborns. The B-b-B methods may be useful for short-term measurements in patients over about 3 years of age, where an added dead space is acceptable and where breathing frequency is relatively low. However, for smaller infants and longer durations of measurements, the method is less practical because of added dead space, gas analyzer response time, critical time alignment between flow and gas signals, and possible condensation of water vapor in the flowmeter.

SUMMARY

The disclosure is based, at least in part, on the discovery that one can determine oxygen consumption with high accuracy in mechanically ventilated subjects, e.g., subjects who have shallow breathing, such as neonates and older patients, by measuring total flow at the inspiratory outlet of the ventilator, corrected for viscosity dependence. Oxygen content of inspiratory gas is determined by flow-weighted averaging for maximum accuracy and precision. Expiratory gas contents of oxygen and carbon dioxide are determined by averaging during expiration. Inspiratory and expiratory gas contents are compared using a time delay that accounts for circuit compliance and bias flow. The techniques use flow-weighting and dynamic time delay, which allow for the accurate determination of oxygen consumption in the single-digit ml/min range at elevated and fluctuating inspired oxygen concentrations, which is typical for many patients including newborns. However, the systems work well for any patients, such as older patients with shallow breathing. The techniques additionally account for the transport delay time of gases travelling between a Y-piece attached to a patient and an expiratory sampling site, to limit the expiratory sampling period. Accounting for this time delay ensures no shift in measured mixed expired gas concentrations caused by alternating gas sampling sites and combines mixed expired concentrations with the measured total flow in the inspiratory limb corrected for gas sample flow.

In some aspects, a computing device-implemented method to determine oxygen consumption in a mechanically ventilated subject includes receiving a signal representing a total flow at an inspiratory outlet of a ventilator, calculating a transport delay time between inspiratory and expiratory gas sample points in a patient ventilation circuitry, transmitting a signal to an inlet selector valve to selectively open a fluid path between the inspiratory gas sample point and an oxygen sensor or between the expiratory gas sample point and the oxygen sensor, receiving data representing oxygen content and carbon dioxide content over a period of time, calculating oxygen consumption data over the period of time from the data representing the total flow, oxygen content and carbon dioxide content and from the transport delay time, and displaying the oxygen consumption data over the period of time.

Implementations may include one or more of the following features: repeating the transmitting and receiving steps over an observation period longer than the period of time. Calculating oxygen consumption comprises calculating a number of whole breaths of a patient from the delay time. Correcting the signal representing the total flow for viscosity dependence. Calculating flow-weighted averages of the inspiratory oxygen content and carbon dioxide content. Calculating a respiratory quotient of a patient. Calculating carbon dioxide production of a patient. Calculating energy expenditure of a patient. Calculating a transport delay time between a Y-connector that is attachable to a patient and the expiratory gas sample point. The subject is a neonate.

In some aspects, a patient ventilation system includes a ventilation fluid circuit with a fluid path connected to sources of air and oxygen, a patient, and a fluid outlet, a flowmeter located in the fluid path between the sources of air and oxygen and the patient, an inhalation fluid sampling line connected at an inhalation gas sample point of the fluid path located between the sources of air and oxygen and the patient, an exhalation fluid sampling line connected to an exhalation gas sample point of the fluid path located between the patient and the fluid outlet or a mixing chamber fluidly connected to the fluid outlet, an oxygen sensor and a carbon dioxide sensor configured to measure an oxygen and a carbon dioxide concentration of a gas passing along a sensing path through the sensor, wherein the sensing path is connected to the inhalation fluid sampling line and to the exhalation fluid sampling line, a selector valve arranged to selectively connect either the inhalation fluid sampling line or the exhalation fluid sampling line to the sensing path, and a computing device comprising a memory configured to store instructions and a processor to execute the instructions to perform operations. These include receiving a signal representing a total flow at an inspiratory outlet of a ventilator, calculating a transport delay time between inhalation and exhalation gas sample points, transmitting a signal to the selector valve to selectively connect either the inhalation fluid sampling line or the exhalation fluid sampling line to the sensing path, receiving data representing oxygen content and carbon dioxide content over a period of time, calculating oxygen consumption data over the period of time from the data representing the total flow, oxygen content and carbon dioxide content and from the transport delay time, and displaying the oxygen consumption data.

Implementations may include one or more of the following features: the inhalation fluid sampling line and/or the exhalation fluid sampling line are water permeable gas tubes that equilibrate their contents to ambient humidity. A portion of the ventilation fluid circuit is inside a ventilator. The computing device performs a further operation comprising calculating a respiratory quotient of the patient. The computing device performs a further operation comprising calculating carbon dioxide production. The computing device performs a further operation comprising calculating an energy expenditure of the patient. The oxygen sensor comprises a laser diode sensor and the carbon dioxide sensor is a nondispersive infra-red sensor.

In some aspects, a computing device-implemented method to determine oxygen consumption in a mechanically ventilated subject includes includes calculating a transport delay time between inhalation and exhalation gas sample points, transmitting a signal to the selector valve to selectively connect either the inhalation fluid sampling line or the exhalation fluid sampling line to the sensing path, receiving data representing oxygen content and carbon dioxide content over a period of time, calculating oxygen consumption data over the period of time from the data representing oxygen content and carbon dioxide content and from the transport delay time, displaying the oxygen consumption data, and calculating a transport delay time between a Y-connector that is attachable to a patient and the expiratory gas sample point.

In some aspects, a patient ventilation system includes a ventilation fluid circuit with a fluid path connected to sources of air and oxygen, a patient, and a fluid outlet, an inhalation fluid sampling line connected at an inhalation gas sample point of the fluid path located between the sources of air and oxygen and the patient, an exhalation fluid sampling line connected to an exhalation gas sample point of the fluid path located between the patient and the fluid outlet or a mixing chamber fluidly connected to the fluid outlet, an oxygen sensor and a carbon dioxide sensor configured to measure an oxygen and a carbon dioxide concentration of a gas passing along a sensing path through the sensor, wherein the sensing path is connected to the inhalation fluid sampling line and to the exhalation fluid sampling line, a selector valve arranged to selectively connect either the inhalation fluid sampling line or the exhalation fluid sampling line to the sensing path, and a computing device comprising a memory configured to store instructions and a processor to execute the instructions to perform operations. These include calculating a transport delay time between inhalation and exhalation gas sample points, transmitting a signal to the selector valve to selectively connect either the inhalation fluid sampling line or the exhalation fluid sampling line to the sensing path, receiving data representing oxygen content and carbon dioxide content over a period of time, calculating oxygen consumption data over the period of time from the data representing oxygen content and carbon dioxide content and from the transport delay time, displaying the oxygen consumption data, and calculating a transport delay time between a Y-connector that is attachable to a patient and the expiratory gas sample point.

The present disclosure describes computing device implemented methods that include calculating a transport delay time between inspiratory and expiratory gas sample points in a patient ventilation circuitry, transmitting a signal to an inlet selector valve to selectively open a fluid path between the inspiratory gas sample point and an oxygen sensor or between the expiratory gas sample point and the oxygen sensor, receiving data representing oxygen content and carbon dioxide content over a period of time, calculating oxygen consumption data over the period of time from the data representing oxygen content and carbon dioxide content and from the transport delay time and displaying the oxygen consumption data over the period of time.

In some embodiments, the methods include repeating the transmitting via receiving steps over an observation period longer than the period of time. Calculating oxygen consumption comprises calculating a number of whole breaths of a patient from the delay time. The method includes receiving a signal representing a total flow at an inspiratory outlet of a ventilator. The method includes correcting the signal representing the total flow for viscosity dependence. Calculating oxygen consumption comprises using the total flow. The method includes calculating flow-weighted averages of the inspiratory oxygen content (and carbon dioxide content if non-zero), calculating a transport delay time between a Y-connector that is attachable to a patient and the expiratory gas sample point, calculating carbon dioxide production of a patient, calculating respiratory quotient of a patient, or calculating energy expenditure of a patient.

Further aspects include patient ventilation systems that include a ventilation fluid circuit with a fluid path connected to sources of air and oxygen, a patient, and a fluid outlet, an inhalation fluid sampling line connected at an inhalation gas sample point of the fluid path located between the sources of air and oxygen and the patient, an exhalation fluid sampling line connected to an exhalation gas sample point of the fluid path located between the patient and the fluid outlet or a mixing chamber fluidly connected to the fluid outlet, a combined oxygen and carbon dioxide sensor configured to measure an oxygen and a carbon dioxide concentration of a gas passing along a sensing path through the sensor, wherein the sensing path is connected to the inhalation fluid sampling line and to the exhalation fluid sampling line, a selector valve arranged to selectively connect either the inhalation fluid sampling line or the exhalation fluid sampling line to the sensing path. The system also includes a computing device with a memory configured to store instructions and a processor to execute the instructions to perform operations of calculating a transport delay time between inhalation and exhalation gas sample points, transmitting a signal to the selector valve to selectively connect either the inhalation fluid sampling line or the exhalation fluid sampling line to the sensing path, receiving data representing oxygen content and carbon dioxide content over a period of time, calculating oxygen consumption data over the period of time from the data representing oxygen content and carbon dioxide content and from the transport delay time, and displaying the oxygen consumption data.

In some embodiments, the inhalation fluid sampling line and/or the exhalation fluid sampling line are water permeable gas tubes that equilibrate their contents to ambient humidity. The systems can include a humidifier that adds water to gas in the inhalation fluid sampling line. A portion of the ventilation fluid circuit is inside a ventilator. The ventilator is attachable to the patient by a Y-connector. A flowmeter is located in the fluid path between the sources of air and oxygen and the patient. Calculating a carbon dioxide production of the patient, calculating a respiratory quotient of the patient or calculating an energy expenditure of the patient can also be included.

The following abbreviations and terms are used herein:
$CO_2$ Carbon dioxide
EXP Expiratory (sampling period)
$F_{exp}CO_2$ Measured expiratory $CO_2$ concentration (fractional)
$F_{exp}O_2$ Measured expiratory $O_2$ concentration (fractional)
$F_E CO_2$ Mixed expired (average) $CO_2$ concentration (fractional)
$F_E O_2$ Mixed expired (average) $O_2$ concentration (fractional)
$F_{inlet}O_2$ Average $O_2$ concentration (fractional) in gas inlet
$F_{insp}CO_2$ Measured inspiratory $CO_2$ concentration (fractional)
$F_{insp}O_2$ Measured inspiratory $O_2$ concentration (fractional)
$F_I CO_2$ Average inspiratory $CO_2$ concentration (fractional)
$F_O O_2$ Average inspiratory $O_2$ concentration (fractional)
I:E ratio Inspiration time/expiration time ratio
INSP Inspiratory (sampling period)
$N_2$ Nitrogen
$N_{breaths}$ Number of breaths
$N_{I-E}$ delay Number of breaths corresponding to I-E time delay
$N_{SKIP,insp,start}$ Breaths to be skipped from analysis in start of INSP period
$N_{SKIP,insp,end}$ Breaths to be skipped from analysis in end of INSP period
$N_{SKIP,exp,start}$ Breaths to be skipped from analysis in start of EXP period
$N_{SKIP,exp,end}$ Breaths to be skipped from analysis in end of EXP period
$O_2$ Oxygen
$P_B$ Barometric pressure
$P_{aw}$ Airway pressure
$PH_2O$ Water vapor pressure
$PH_2O_{sat}(t)$ Saturated water vapor pressure at temperature t
$P_{peak}$ Peak airway pressure
$P_{PEEP}$ PEEP (positive end-expiratory pressure)
$P_{trig\ \%,vent}$ Airway pressure trigger level in percent of peak-peak pressure
REE Resting energy expenditure
$RH_{amb}$ Ambient relative humidity
$RH_{exp}$ Relative humidity in expired gas
RQ Respiratory quotient
$RQ_{init}$ Initial respiratory quotient
RR Respiratory rate
$t_{amb}$ Ambient temperature
$t_{exp}$ Temperature in expired gas
$T_E$ Expiration time
$T_{FGD,I}$ Flow-gas delay time, inspiratory gas sample line
$T_{FGD,E}$ Flow-gas delay time, expiratory gas sample line
$T_{flush}$ Gas sample line flushing time (in addition to $T_{FGD}$)
$T_I$ Inspiration time
$T_{I-E\ delay}$ I-E delay time
$T_{INSP}$ Inspiratory sampling period
$T_{INSP,a}$ First part of $T_{INSP}$ corresponding to the length of $T_{EXP}$
$T_{INSP-EXP}$ Transport time between inspiratory and expiratory sampling points
$V'_{bias}$ Expiratory bias/Insp. trigger flow rate
$V'_{bias,e}$ Effective bias flow rate
$V'_{compl}$ Volume flow due to compliance effect
$V'CO_2$ Carbon dioxide production
$V_{DS,E}$ Volume of expiratory limb
$V_{DS,I}$ Volume of inspiratory limb
$V_{DS,I-Y}$ Volume between inspiratory sample point and Y-piece
$V_{DS,M}$ Volume of mixing chamber (to gas sample point)
$V_{DS,V}$ Internal volume of ventilator's expiration channel
$V_{DS,Tub}$ Compressible volume of tubing
$V_{DS,Tot}$ Total volume between inspiratory and expiratory sample points
$V'_E$ Expiratory minute ventilation
$V'_{E,tot}$ Total expiratory minute ventilation incl. $V'_{bias,e}$ and $V'_{compl}$
$V'_{gas\ sample}$ Gas analyzer sampling flow rate
$V'_I$ Inspiratory minute ventilation
$V'_{I,tot}$ Total inspiratory minute ventilation incl. $V'_{bias,e}$ and $V'_{compl}$
$V'_{insp}$ Inspiratory flow (instantaneous)
$V_{INSP-EXP}$ Circuit volume between inspiratory and expiratory sampling points
$V_{Y-EXP}$ Circuit volume between Y-piece and expiratory sampling points
$V'O_2$ Oxygen uptake
$V'O_{2,init}$ t Initial oxygen uptake
$V_T$ Tidal volume
$\Delta_t$ Sample period As used herein, "$V'O_2$" and "$VO_2$," for example, refer to the same parameter.

The disclosure provides several advantages over a conventional bag system, including accurate flow-weighted $F_I O_2$ determination on the inspiratory side as opposed to time-weighted (arithmetic average) estimates that make the system insensitive to fluctuations in $F_I O_2$ from the ventilator. There is no mixing chamber needed in the inspiratory circuit.

The details of one or more embodiments of the invention are set forth in the accompanying drawings and the description below. Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

The methods and apparatus described herein can determine oxygen consumption ($V'O_2$) in mechanically ventilated subject, including neonates, by sampling inspired and expired gas and measuring inspiratory flow. Unlike other techniques, these techniques are suitable for use in mechanically ventilated pediatric patients including neonates and premature infants where ventilation is low and respiratory rates are high. Oxygen content of inspiratory gas is determined by flow-weighted averaging for maximum accuracy and precision. Expiratory gas contents of oxygen and carbon dioxide are determined by averaging during expiration. Inspiratory and expiratory gas contents are compared using a time delay, which accounts for circuit compliance and bias flow.

The technique additionally accounts for the transport delay time of gases travelling between a Y-piece attached to a patient and an expiratory sampling site, to limit the expiratory sampling period. Accounting for this time delay ensures no shift in measured mixed expired gas concentrations caused by alternating gas sampling sites and combines mixed expired concentrations with the measured total flow in the inspiratory limb corrected for gas sample flow. The flow-weighting and dynamic time delays allow accurate determination of oxygen consumption in the single-digit ml/min range at the fluctuating inspired oxygen concentrations typical for ventilators used for newborns and other patients.

Ventilator Systems

The new systems overcome several compounding errors in oxygen consumption measurements. First, ventilators are known to deliver fluctuating oxygen concentrations ($F_IO_2$), which can have significant effects on metabolic measurements. By compensating measures of inspiratory flow of dry gas for $F_IO_2$-dependent changes in viscosity and flow-weighting $F_IO_2$ measurements (rather than simple time-weighted estimates, as other current instruments do), it is possible to determine both inspired volume flow and average $F_IO_2$ accurately and make the measurement relatively insensitive to fluctuations in $F_IO_2$ from the ventilator.

Expired concentrations are measured at the exhaust port of the ventilator to obtain reliable average estimates. By combining inspired flow and $F_IO_2$ with time shifted $F_EO_2$ and $F_ECO_2$, it is possible to determine expired flow, $V'O_2$, $V'CO_2$, RQ, and REE. The system also accounts for the presence of bias flow (used to enable flow triggering of patient breaths in modern ventilators), uses a lower sampling rate (60 mL/min) than any device on the market, and can account for higher sampling rates as well. The system also measures respiratory quotient and resting energy expenditure, which helps in understanding how many calories the patient consumes over time. One can titrate how much nutrition the patient should receive based on this information, which could decrease time on ventilator in the ICU.

Figure 1:
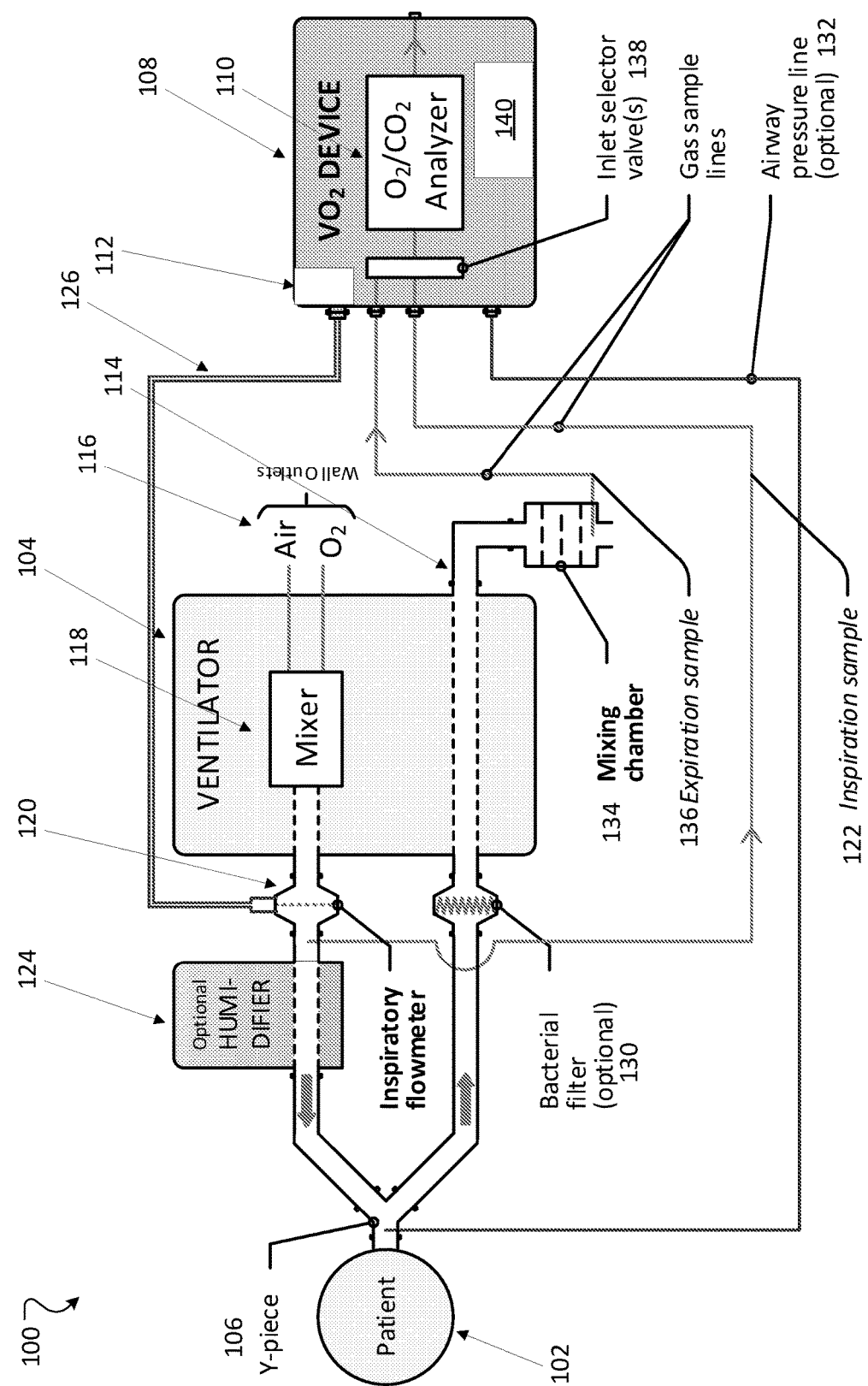
FIG. 1 is a schematic of a system with a specialized device for accurate measurement of oxygen consumption.

FIG. 1 shows a $VO_2$ system 100 for taking oxygen consumption measurements in newborns, such as patient 102. The patient 102 is connected to a conventional ventilator 104 using a Y-piece attachment 106, as is typically done in treatment centers and with typically available equipment. The $VO_2$ system 100 enables the patient 102 to use a novel $VO_2$ device 108 that includes an $O_2/CO_2$ sensor 110 that has an $O_2$ sensor (e.g., a laser diode sensor) with $CO_2$ module (e.g., a nondispersive infrared sensor or NDIR) and a differential pressure sensor 112.

The ventilator 104 is connected to air and $O_2$ sources 116. The air and $O_2$ are mixed in the ventilator in a mixer 118. The mixed air and oxygen flow out of the ventilator 104 and are measured by an inspiratory flowmeter 120, which can be a differential pressure type pneumotach, e.g., a device with a screen inserted in the fluid flow that creates a known pressure drop directly proportional to the fluid velocity. The flowmeter 120 is connected to the $VO_2$ device 108 using double-lumen rubber tubing 126 and is used for taking measurements at the flowmeter 120 to the device 108. The mixed air and $O_2$ in the inspiration line is sampled and the sample is carried to $O_2/CO_2$ sensor 110 via inspiration sampling line 122. The mixed $O_2$/air then flows through an optional humidifier 124 that adds a controlled amount of water to the mix. The inspiration sampling line 122 takes a sample before the humidifier 124, so that the $O_2$/air mixture sample is upstream of the humidifier 124. The sample taken at the upstream sampling point is therefore dry inspiratory gas, which is analyzed by the $O_2/CO_2$ sensor 110. In some embodiments, the inspiration sampling line 122 can be downstream of the humidifier 124.

The humidified air/$O_2$ mix flows into the patient 102 via one branch of the Y-piece attachment 106 and then back out through the second branch of the Y-piece attachment 106. The pressure of the expiration gas can be measured at the Y-piece attachment 106 via pressure line 132, or another place in the inspiratory limb of the circuit. The expired gas passes through an optional bacterial filter 130, and back through the ventilator 104 and out through the ventilator exit port 114. A small mixing chamber 134 may be attached to the ventilator exit port 114 and mixes the expired gas as it exits the ventilator 104. A sample of the expiration gases is diverted from the mixing chamber 134 or exit port via expiration sampling line 136 and measured by the $O_2/CO_2$ sensor 110 of the $VO_2$ device 108.

The $VO_2$ device 108 includes an inlet selector valve 138 (e.g., a solenoid valve or pinch valve) controlled by a controller 140 to automatically alternate between inspiratory (INSP) and expiratory (EXP) gas measurements.

The tubes connecting the $VO_2$ device 108 and inspiration fluid circuit (i.e., the inspiration sampling line 122 for measurement of the inspired oxygen concentration $F_IO_2$) and between the $VO_2$ device 108 and the output of the mixing chamber (i.e., expiration sampling line 136 for measurement of mixed expired oxygen concentration $F_EO_2$), respectively are preferably water-permeable tubes, such as Nafion® gas sample tubes. Nafion® gas sample tubes are water permeable gas tubes that equilibrate their contents to ambient humidity. This equilibration is particularly important on the expiration line, because the measurement is downstream of the humidifier 124 and the patient 102 and may be fully saturated. Saturated gas can cause "rain-out" where the tubing sampling gas from the expiration line becomes wet from condensation, which distorts subsequent readings. The water permeability and a chemical reaction inside the Nafion® gas sample tubes eliminate this problem.

The $VO_2$ device 108 connects to normal ventilator circuitry in a manner similar to that of available devices on the market. The $VO_2$ system 108 is different from such devices in that the $O_2/CO_2$ sensor 110, inspiration gas sample line 122, and expiration gas sample line 136 are connected at the ventilator ports, remote from the proximal Y-piece 106. This feature avoids the addition of dead space, and also the risks associated with a weighted sensor attached to a small tracheal tube, which risks displacement. The technique is based on sampling of inspired and mixed expired gas and measurement of inspiratory flow. Unlike other techniques, this technique is suitable for use in mechanically ventilated pediatric patients where minute ventilation is low, metabolic rate is low (e.g., 5 or 10 ml/min) and respiratory rates are high (e.g., 60 or 80 bpm).

The $VO_2$ system 100 determines both inspired volume flow ($V'_I$) and average $F_IO_2$ accurately, effectively coping with fluctuations in $F_IO_2$ from the ventilator 104. The $VO_2$ system 100 measures inspiratory flow of dry gas corrected for changing viscosity when $F_IO_2$ changes, and flow-weighted $F_IO_2$ corrected for flow-gas delay. Expired concentrations ($F_EO_2$ and $F_ECO_2$) are measured at the outlet of the mixing chamber 134. By combining $V'_I$, $F_IO_2$ and $F_ICO_2$ (which is generally close to zero) with time shifted $F_EO_2$ and $F_ECO_2$ it is possible to determine $V'_E$, $V'O_2$, $V'CO_2$, as well as derived parameters including respiratory quotient (RQ) and resting energy expenditure (REE) of the patient.

Once the patient 102 is attached to the ventilator 104 via the Y-piece attachment, the inlet selector valve 138 is set to the INSP position by the controller 140, and the inlet is flushed. $O_2$ concentration is measured over one or more complete respiratory cycles as determined by the flowmeter 120. This is measured with the flow-gas delay taken into account (as discussed below). The instantaneous flow is measured at the same time.

Thereafter, the inlet selector valve 138 switches to the EXP position and the EXP inlet is flushed. $O_2$ and $CO_2$ concentrations are measured, preferably over one or more complete respiratory cycles as determined e.g. by the flowmeter 120.

The oxygen uptake, or $V'O_2$, is calculated as the amount of oxygen extracted from the inspired gas per minute. As discussed in detail below, this is the difference between the oxygen volume inspired and expired divided by time, taking into account the inspiration/expiration delay when comparing inspired and expired values. The system then repeats the steps for as long as monitoring is required.

Using the $VO_2$ system 100, the patient 102 does not need to breathe through a specialized device, but rather is attached to a standard ventilator. Prior systems use a mixed expired technique where no sensors are attached proximal to the patient, however, system 100 measures inspired flows rather than concentrating on just expiration with an expiration meter that measures wet gas. Instead, the system measures the flow of inspired gas, which is always dry. Since gas concentration from a ventilator is not steady and fluctuates a great deal the inspired average concentration is determined, rather than simply the instantaneous concentration. As gas flow and concentrations both change over time, a simple arithmetic mean is insufficient for accuracy; the system uses a flow-weighted average to take the flow into account. In prior systems, oscillations of ±2% $O_2$ are too high to make accurate measurements without flow-weighted averaging. Now fluctuations are compensated for by flow-weighted averaging.

Ventilator Software

Software for controlling the $VO_2$ system 100 can be stored on and executed by the controller 140, and can include setup, calibration, and measurement options.

Figure 2:
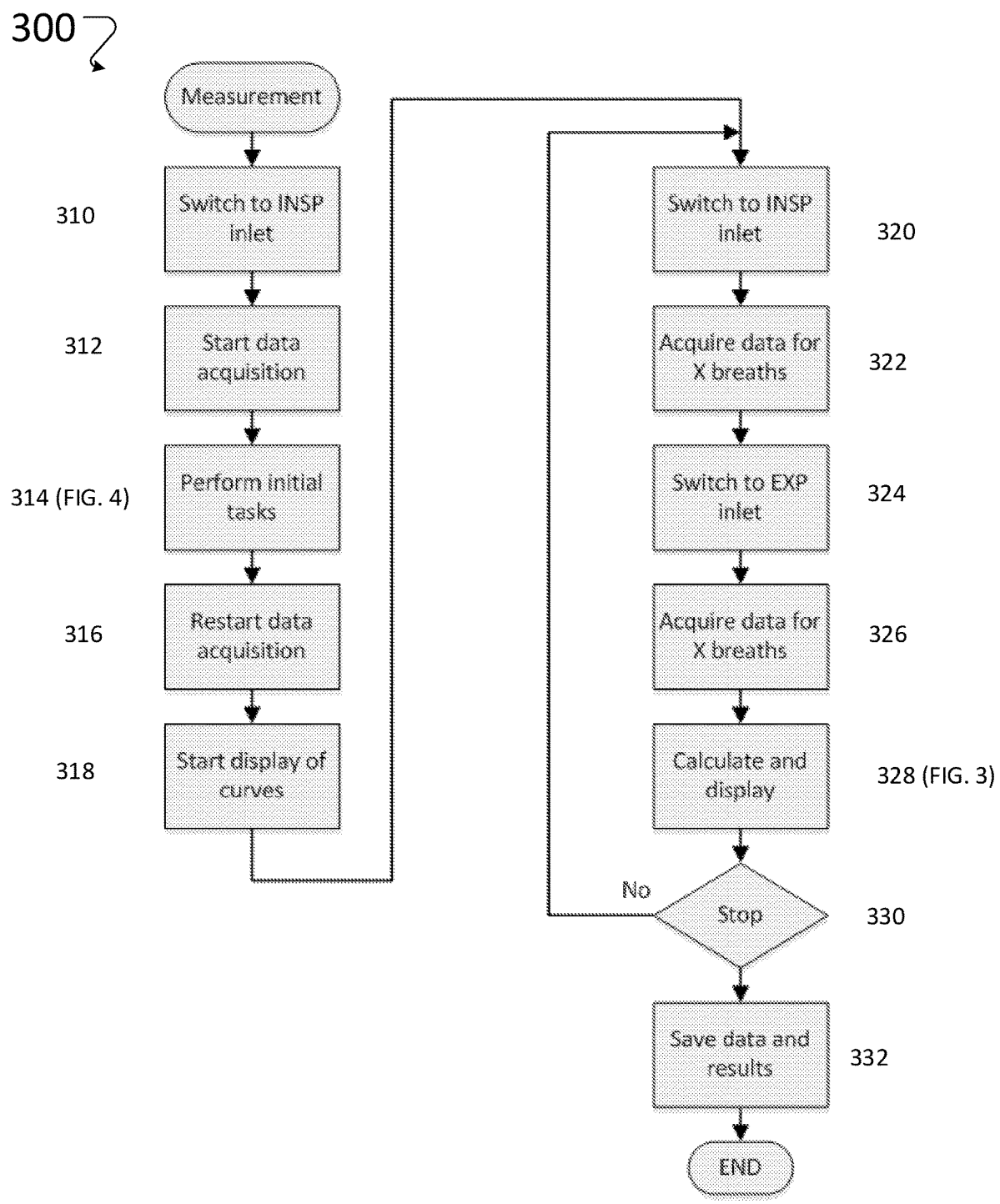
FIG. 2 is a flowchart that shows a measurement sequence to be used for control, data acquisition and calculation.

The flow chart in FIG. 2 shows the measurement sequence 300 used for control, data acquisition, and calculation. To take a measurement, the software sequence 300 causes the controller 140 to send a signal to the inlet selector valve 138 to switch to the INSP inlet (step 310) and then starts data acquisition (step 312). The system then performs initial tasks as detailed in FIG. 4 (step 314) and restarts data acquisition (step 316). Curves representing the data are displayed (step 318), and the system switches to INSP inlet (step 320) and acquires data for a desired number (e.g., 5-10) of breaths at step 322 and switches to the EXP inlet (step 324) and acquires data for a desired number of breaths at step 326. The concentrations, flows, and other parameters are calculated (as described in detail with respect to FIG. 3) and displayed at step 328. When sufficient data has been acquired, the system saves the data and results and ends the measurement. If more data is desired, e.g., for long-term monitoring, the system returns to step 320 and switches back to the INSP inlet and repeats the steps.

Figure 4:
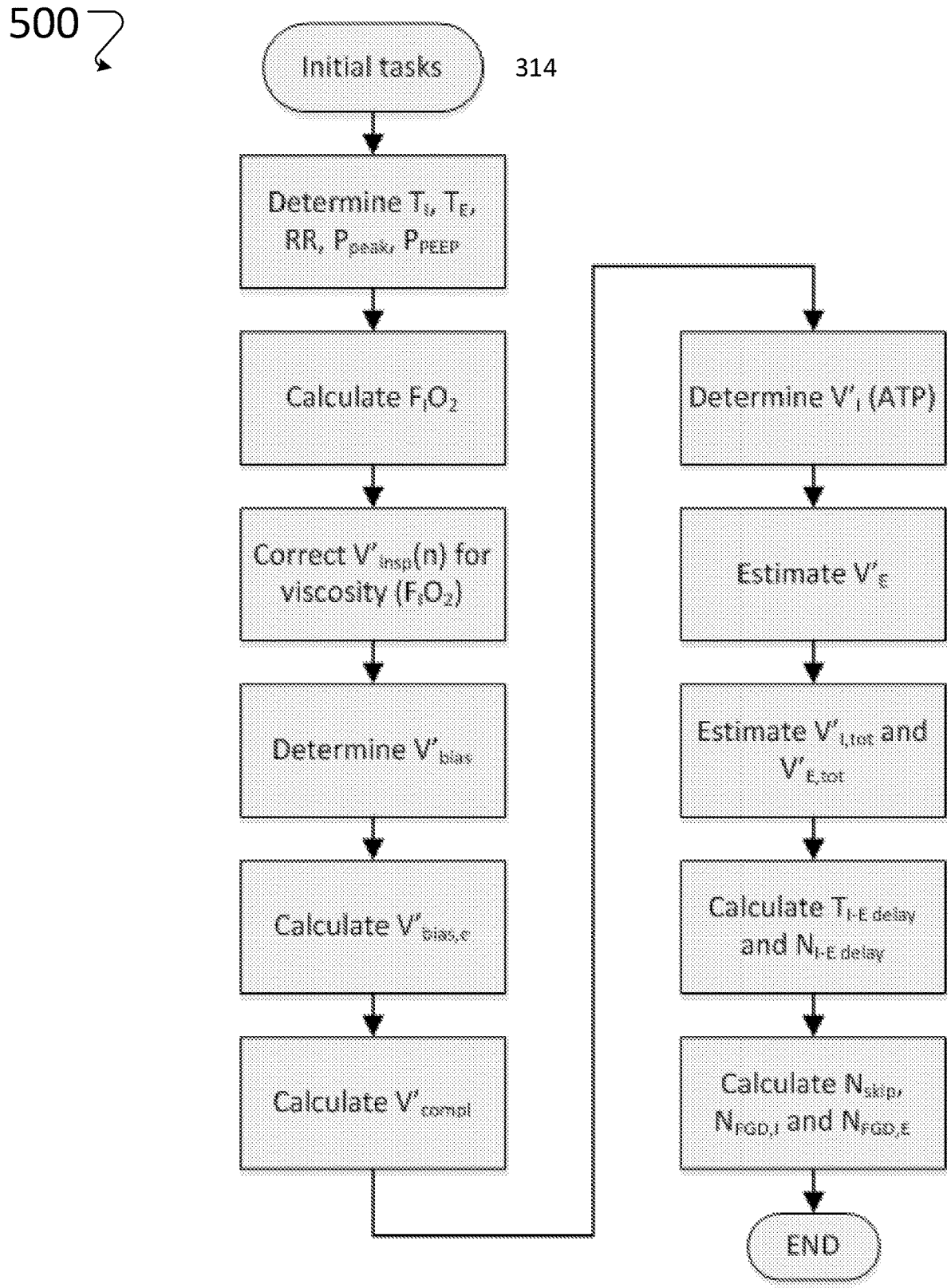
FIG. 4 is a flowchart that shows the initial tasks to determine the transport delay.
Figure 5:
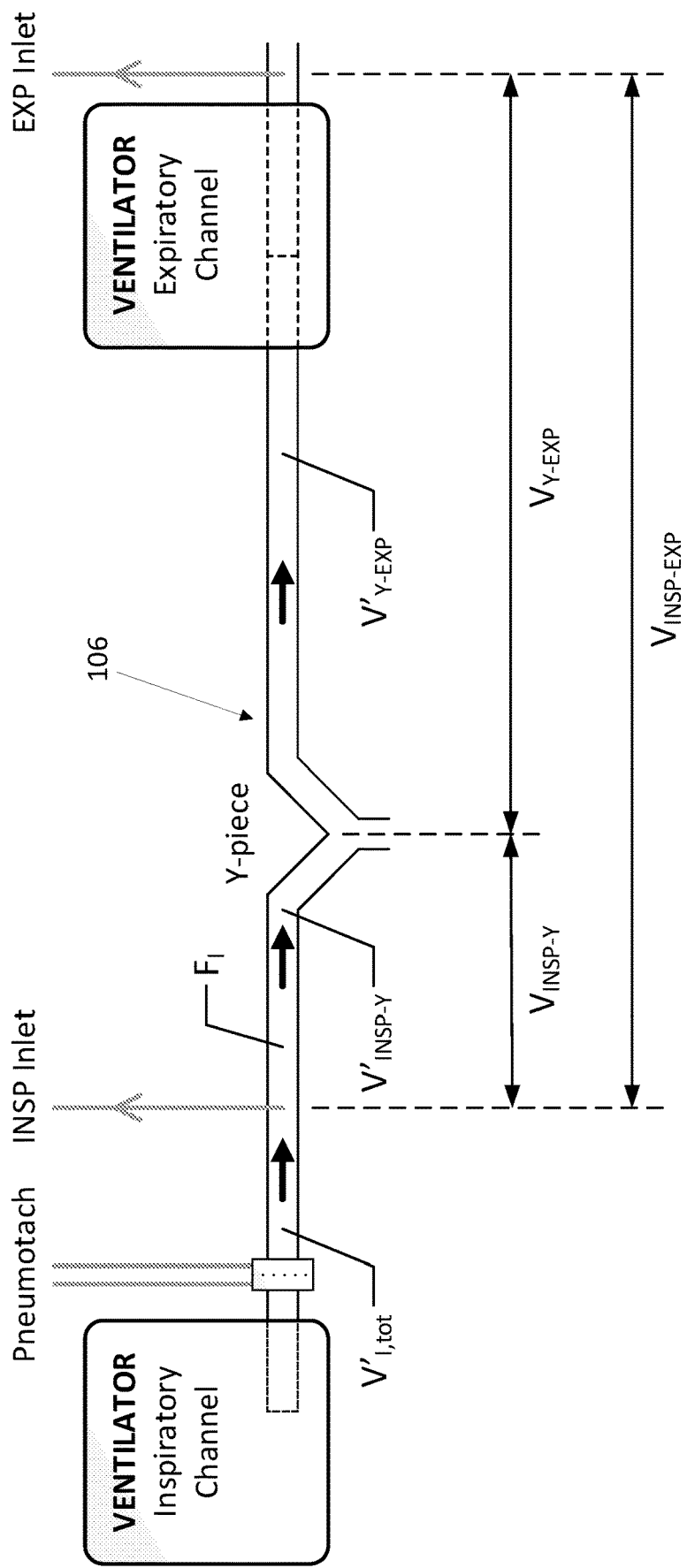
FIG. 5 an explanatory schematic of the portion of the inspiratory and expiratory tubing near the Y-piece for defining circuit volumes.

As discussed in relation to FIGS. 5 and 6, the optimum number of breaths ("X breaths") in steps 322 and 326 of FIG. 2 may be different, and during non-steady conditions the optimum number of breaths should be determined continuously based on the actual flow rate $V'_{I,tot}$, and known circuit volumes by integration of flow from breath to breath using the appropriate steps from step 328, and not only as part of the initial tasks (step 314 and FIG. 4).

Figure 3:
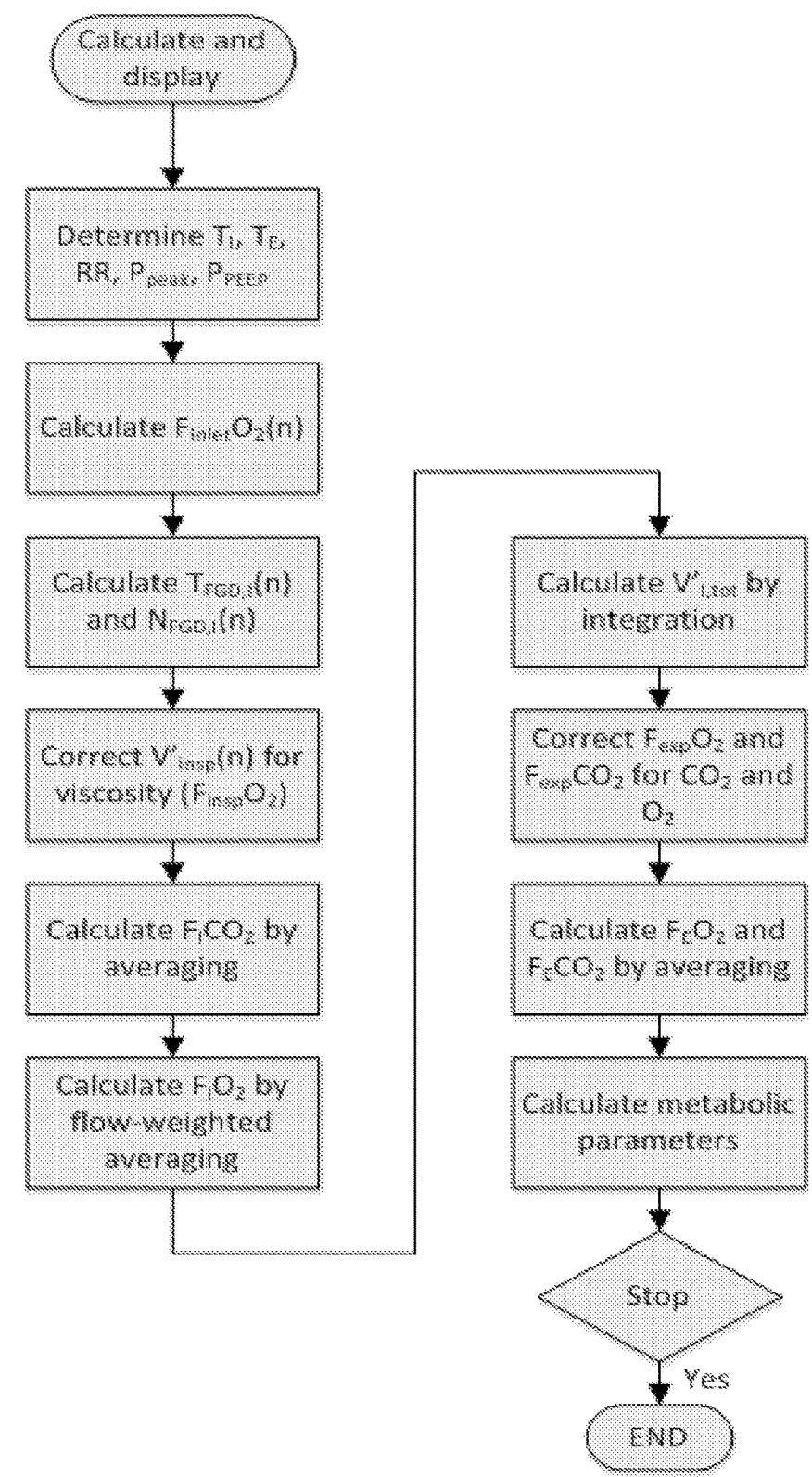
FIG. 3 is a flowchart that shows the calculations for a respiratory cycle comprising measurements from the inspiratory and expiratory gas sample inlets.

The flow chart in FIG. 3 shows the calculation and display steps 400 in detail for each cycle comprising measurements from the inspiratory and expiratory gas sample inlets, respectively, which are the details of step 328 in the flow chart of FIG. 2.

Oxygen consumption is calculated using the equations below. Components are average values, appropriately adjusted for the inspiration-expiration (I-E) delay time. The I-E delay is the transport delay in the patient circuitry between inspiratory and expiratory gas sample points (truncated corresponding to a whole number of breaths).

The following 3 basic equations assume that the $N_2$ exchange is zero (steady-state, equation 1):

$$V'_E = V'_I - V'O_2 + V'CO_2 \tag{1}$$

$$V'O_2 = V'_I \times F_IO_2 - V'_E \times F_EO_2 \tag{2}$$

$$V'CO_2 = V'_E \times F_ECO_2 - V'_I \times F_ICO_2 \tag{3}$$

In these and the following equations all flows (V') are given at the same conditions (e.g., "STPD," which stands for standard temperature and pressure, dry; oxygen consumption; and carbon dioxide production are standardized to standard temperature (0° C.), barometric pressure at sea level (101.3 kPa) and dry gas) and all concentrations F are fractional concentrations of dry gas as measured using the Nafion® tubing.

Substituting $V'_E$ from equation 1 into equations 2 and 3 gives:

$$V'_I \times F_I O_2 = V'O_2 + (V'_I - V'O_2 + V'CO_2) \times F_E O_2 \quad (4)$$

$$V'_I \times F_I CO_2 + V'CO_2 = (V'_I - V'O_2 + V'CO_2) \times F_E CO_2 \quad (5)$$

Rearranging Each Equation Gives:

$$(1 - F_E O_2) \times V'O_2 + (F_E O_2) \times V'CO_2 = (F_I O_2 - F_E O_2) \times V'_I \quad (6)$$

$$(F_E CO_2) \times V'O_2 + (1 - F_E CO_2) \times V'CO_2 = (F_E CO_2 - F_I CO_2) \times V'_I \quad (7)$$

As $V'_I$ and all fractional concentrations are measured and therefore known, these are two equations in two unknowns, $V'O_2$ and $V'CO_2$, which can be solved:

$$V'O_2 = V'_I \times \frac{F_I O_2 \times (1 - F_E CO_2) - F_E O_2 \times (1 - F_I CO_2)}{1 - F_E O_2 - F_E CO_2} \quad (8)$$

$$V'CO_2 = V'_I \times \frac{F_E CO_2 \times (1 - F_I O_2) - F_I CO_2 \times (1 - F_E O_2)}{1 - F_E O_2 - F_E CO_2} \quad (9)$$

The denominator is the fractional concentration of nitrogen. It appears as the amounts of nitrogen in inspired and expired gas at steady-state are assumed to be equal. Therefore, these equations can also be derived using the Haldane transformation, $V'_I \times F_I N_2 = V'_E \times F_E N_2$, instead of equation 1.

Using the Haldane transformation ($V'_1 \times F_I N_2 = V'_E \times F_E N_2$) and the equations 9a and 9b together with equations (2) and (3) can also be used to directly derive equations 8 and 9:

$$F_I N_2 = 1 - F_I CO_2 - F_I O_2 \quad (9a)$$

$$F_E N_2 = 1 - F_E CO_2 - F_E O_2 \quad (9b)$$

Substituting $V'O_2$ and $V'CO_2$ according to equations 8 and 9 into equation 1 gives:

$$V'_E = V'_I \times \frac{1 - F_I O_2 - F_I CO_2}{1 - F_E O_2 - F_E CO_2} \quad (10)$$

These equations (and the method) become less accurate when used when breathing close to 100% $O_2$ as the denominator would be close to zero. The method becomes more prone to gas measurement errors as the oxygen concentration increases.

The respiratory quotient is determined:

$$RQ = \frac{V'CO_2}{V'O_2} \quad (11)$$

Inspiratory minute ventilation $V'_I$ is determined by integration of inspiratory flow over one or more complete breaths:

$$V'_I = \frac{\sum_{n=0}^{N-1} V'_{insp}(n)}{N} \quad (12)$$

where $V'_{insp}(0)$ and $V'_{insp}(N-1)$ are the first and last inspiratory flow samples, respectively, in a breath (or a sequence of breaths).

A reliable average $F_I O_2$ estimate (allowing for $F_I O_2$ fluctuations at the inspiratory outlet of the ventilator) is obtained by flow-weighted averaging:

$$F_I O_2 = \frac{\sum_{n=0}^{N-1} F_{insp} O_2(n) \times V'_{insp}(n)}{\sum_{n=0}^{N-1} V'_{insp}(n)} \quad (13)$$

$F_I CO_2$ is determined in the same way as $F_I O_2$ by replacing $F_{insp} O_2$ with $F_{insp} CO_2$ in equation 13 (or calculated as an arithmetic mean or set to zero).

$F_E O_2$ is calculated as a time-weighted average value (preferably during expiration(s) only, i.e. when $V'_{insp}$ is zero or equal to the bias flow in case of bias flow, $V'_{bias}$):

$$F_E O_2 = \frac{\sum_{m=0}^{M-1} F_{exp} O_2(m)}{M} \quad (14)$$

Likewise for $F_E CO_2$:

$$F_E CO_2 = \frac{\sum_{m=0}^{M-1} F_{exp} CO_2(m)}{M} \quad (15)$$

Inspiratory minute ventilation $V'_I$ is corrected from atmospheric temperature and pressure (ATP) to STPD assuming that inspired gas flow (as measured) is at ambient temperature:

$$V'_I(STPD) = V'_I \times \frac{273}{273 + t_{amb}} \times \frac{P_B - P_{H_2O,insp}}{760} \quad (16)$$

$P_{H2O,insp}$ may be set to zero if inspiratory gas from ventilator is dry, as follows:

$$V'_I(STPD) = V'_I \times \frac{273}{273 + t_{amb}} \times \frac{P_B}{760} \quad (17)$$

Average fractional concentrations of dry gas and $V'_I$ (STPD) can now be inserted into equations 8 and 9 to yield STPD values of $V'O_2$ and $V'CO_2$.

The BTPS (body temperature and pressure, saturated: volumes and flows are standardized to barometric pressure, body temperature, saturated with water vapor) value of $V'_E$ is determined by correcting $V'_I$ from STPD to BTPS in equation 10:

$$V'_E(BTPS) = V'_I(STPD) \times \frac{310}{273} \times \frac{760}{P_B - 47} \times \frac{1 - F_I O_2 - F_I CO_2}{1 - F_E O_2 - F_E CO_2} \quad (18)$$

All fractional concentrations used in calculations must be time-shifted corresponding to the transit and rise time (response time) between instantaneous flow and delayed gas measurement:

$$F(n) = F_{meas}(n + n_{delay}) \quad (19)$$

$n_{delay}$ is corrected for the influence of viscosity. This is particularly important in equation 12, which can be rewritten:

$$F_I O_2(n) = \frac{\sum_{n=0}^{N-1} F_{insp} O_2(n + n_{delay}) \times V'_{insp}(n)}{\sum_{n=0}^{N-1} V'_{insp}(n)} \quad (20)$$

Assuming that inspiratory gas composition (oxygen concentration) is measured close to the flowmeter 120, measured flow rates can be corrected for changes in viscosity of the inspired gas mixture (assuming a Lilly-type pneumotachometer).

Inspired gas consists of $O_2$ and $N_2$. Since the inspired oxygen concentration delivered by the ventilator is almost constant for longer periods, it is adequate to correct each estimate of $V'_I$ (and not $V'_{insp}$). The correction presumes that the flow calibration is done using atmospheric air. For each respiratory cycle a viscosity gain factor is calculated and used for correction of the measured flow.

The viscosity gain factor is calculated as:

$$G_{flow} = \frac{\mu_{air}}{\mu_{insp}} \quad (21)$$

Corrected inspired flow rate (inspired minute ventilation) is calculated as:

$$V'_{I,corr} = V'_I \times G_{flow} \quad (22)$$

$V'_{insp}$ is corrected for $P_{insp}$ and $t_{insp}$ in order to obtain $V'_I$ at STPD:

$$V'_I(STPD) = \frac{\sum_{n=0}^{N-1} V'_{insp}(n) \times \frac{273}{273 + t_{insp}} \times \frac{P_{insp} - P_{H_2O,insp}}{760}}{N} \quad (23)$$

$P_{H_2O,insp}$ is set to zero and $t_{insp}$ is constant (dry inspiratory gas at constant temperature from ventilator) in the following:

$$V'_I(STPD) = \frac{\sum_{n=0}^{N-1} V'_{insp}(n) \times \frac{P_{insp}}{760}}{N} \times \frac{273}{273 + t_{insp}} \quad (24)$$

Since the inspiratory gas sample point is downstream from the flow measurement site the gas sample flow must be subtracted from the measured $V'_I$:

$$V'_{I,corr} = V'_I - V'_{gas\ sample} \quad (25)$$

The gas sample flow is the sum of inspiratory and optional airway sample flow.

Correction of expiratory minute ventilation, $V'_E$, for bias flow is:

$$V'_{E,corr} = V'_E - V'_{bias} \times \frac{T_E}{T_I \times T_E} \quad (26)$$

In equations 8-10, where both inspired (I) and expired (E) flows and fractional concentrations appear, an I-E delay time must be applied in order to provide the best possible correction when $F_I O_2$ or $V'_I$ is changing. It is reasonable to apply an I-E delay correction on a whole breath basis only, i.e. to determine the number of tidal volumes in the circuitry between inspiratory and expiratory gas sample points:

$$\Sigma_{i=1}^{N_{breaths,I-E}} V_T(i) \geq V_{circuit} \quad (27)$$

$N_{breaths,I-E}$ only needs to be recalculated when a significant change in $V'_I$ is detected.

The flow chart in FIG. 4 shows the sequence 500 of initial tasks to determine the inspiration-expiration (I-E) delay needed to compare the inspired and expired gas (step 314 of FIG. 2). The system 100 includes a timing algorithm that compensates for this delay, which otherwise can result in up to 10-20% error depending on gas sampling flow and total flow delivered by the ventilator. The system therefore must determine the time it takes for gas to travel along the fluid circuit, and alternate between two sample points while taking into account this time period.

This latter time shift must be taken into account when comparing inspired and expired gas concentrations in the calculation of $V'O_2$, etc. To do so, it is assumed that the concentrations $F_E$ and the flow in the expiratory limb (equal to $V'_{I,tot}$ if assuming an RQ of 1) match each other (i.e., have been measuring for a very long time using the EXP inlet). Gas sampling is switched to the INSP inlet. All the gas downstream from the INSP inlet will now move at a lower speed ($V'_{I,tot} - V'_{gas\ sample}$).

Gas contained in the expiratory limb after the Y-piece will now move towards the EXP inlet at this lower speed. At the same time, gas entering the expiratory limb at the Y-piece will now change average concentrations corresponding to the lower flow ($V'_{I,tot} - V'_{gas\ sample}$), e.g., to a higher $F_E CO_2$ and lower $F_E O_2$ (higher $\Delta F$).

Gas is sampled from the INSP inlet during a period $T_{INSP}$, after which the system is switched back to the EXP inlet and sample taken from this inlet during a period $T_{EXP}$. All the gas downstream from the INSP inlet will now move at the higher speed $V'_{I,tot}$.

Referring to FIG. 5, which shows the relevant circuit volumes at or near the Y-piece attachment 106 to ensure constant concentrations $F_E$ measured during the entire period $T_{EXP}$, the period $T_{INSP}$ must be long enough to ensure that the circuit between the Y-piece and the EXP inlet has been flushed with the flow $V'_{I,tot} - V'_{gas\ sample}$. This can be expressed by the following criterion:

$$T_{INSP} \geq \frac{V_{Y-EXP}}{V'_{I,tot} - V'_{gas\ sample}} \quad (28)$$

At the same time, the period $T_{EXP}$ must be shorter than the time it takes to flush the circuit between the Y-piece and the EXP inlet with the flow $V'_{I,tot}$. This can be expressed by the following criterion:

$$T_{EXP} \leq \frac{V_{Y-EXP}}{V'_{I,tot}} \quad (29)$$

Also, we are aiming at $T_{INSP}=T_{EXP}$ to compare essentially the same sample of gas from the inspiratory and expiratory limbs, which, however, is not possible according to the inequalities for $T_{INSP}$ and $T_{EXP}$ from which it follows that $T_{INSP}>T_{EXP}$.

A solution which would work at both low ventilations (where the gas sample flow constitutes a significant part of the total flow in the circuit) and high ventilations (where total flow is high with resulting short cycle times according to the above) is one in which the sampling periods $T_{INSP}$ and $T_{EXP}$ both meet the requirements according to the inequalities above to ensure constant mixed expired concentrations during $T_{EXP}$, but the period used for averaging during the INSP period can be shortened by using only the first part of $T_{INSP}$ corresponding to the length of $T_{EXP}$ ($T_{INSP,a}$), and making sure that the spacing between the periods is equal to $T_{INSP-ExP}$, where $$T_{INSP-EXP} = \frac{V_{INSP-EXP}}{V'_{I,tot} - V'_{gas\ sample}} \quad (30)$$

Accounting for the gas transport time $T_{INSP-EXP}$ allows the quantification of $O_2$ and $CO_2$ concentrations on essentially the same sample of gas from the inspiratory and expiratory limbs.

When ensuring that the $T_{INSP}$ and $T_{EXP}$ inequalities are met there should be no need to skip breaths or data in the end of each sampling and analysis period.

To flush the gas sample tubes after switching, data corresponding to the flow-gas delay time (gas sample tube flush time) should be excluded from the analysis. Inlet flushing may be of limited importance during steady conditions, but as a minimum the common internal tubing between solenoid and measurement cells must be flushed.

Additional flushing (skip of breaths) may be used to account for diffusion/mixing of gases and circuit volume uncertainties during the transitions.

The optimal solution can be summarized as:
INSP sampling period:

$$T_{INSP} = T_{INSP-EXP} = \frac{V_{INSP-EXP}}{V'_{I,tot} - V'_{gas\ sample}} \quad (31)$$

EXP sampling period:

$$T_{EXP} = \frac{V_{Y-EXP}}{V'_{I,tot}} \quad (32)$$

INSP analysis period:

$$T_{INSP,a} = T_{EXP} \quad (33)$$

Spacing between analysis periods:

$$T_{INSP-EXP} = T_{NSP} \quad (34)$$

| | |
|---|---|
| $N_{SKIP,\ insp,\ start}$ | Corresponds to the flow-gas delay time |
| $N_{SKIP,\ insp,\ end}$ | Zero |
| $N_{SKIP,\ exp,\ start}$ | Corresponds to the flow-gas delay time |
| $N_{SKIP,\ exp,\ end}$ | Zero (or a manually entered value to account for volume uncertainties) |

The program performs initial calculations according to sequence 500. In detail, the first step is to determine $T_I$ and $T_E$ from the airway pressure signal $P_{aw}$ as average values of $T_I$ and $T_E$ from a number of respiratory cycles.

Then the system determines $P_{peak}$ from the airway pressure signal $P_{aw}$ as the average value of a number of $P_{peak}$ values, each determined during a respiratory cycle.

The system then determines $P_{PEEP}$ from the airway pressure signal $P_{aw}$ as an average value of $P_{aw}$ measured in each expiration over a number of respiratory cycles.

The system then determines $F_IO_2$ as an average value of $F_{insp}O_2$ measured over a number of respiratory cycles.

Then correcting the inspiratory flow signal $V'_{insp}$ for viscosity ($F_IO_2$):

$$V'_{insp,corr}(n) = V'_{insp}(n) \times G_{flow} \quad (35)$$

Thereafter, the system determines $V'_{bias}$ from the inspiratory flow signal $V'_{insp}$ as an average value of $V'_{insp}$, corrected for viscosity ($F_IO_2$), $V'_{insp,corr}$, measured in each expiration over a number of respiratory cycles.

The system then calculates RR as an average value:

$$RR = \frac{1}{T_I + T_E} = \frac{60\ s/min}{T_I + T_E} \quad (36)$$

The system then calculates the effective bias flow (at ATP):

$$V'_{bias,e} = V'_{bias} \times \frac{1}{\frac{T_I}{T_E} + 1} \quad (37)$$

Thereafter, the system calculates the compliance effect (at atmospheric temperature and pressure, ATP):

$$V'_{compl} = (V_{DS,I} + V_{DS,E}) \times \frac{(P_{peak} - P_{PEEP}) \times \frac{760}{1033.2}}{P_B} \times RR \quad (38)$$

The system can also determine inspired minute ventilation $V'_I$ (at ATP) as an average value by integration of inspiratory flow $V'_{insp}$, corrected for viscosity ($F_IO_2$), $V'_{insp,corr}$ over a number of consecutive respiratory cycles as follows:

$$V'_I = \frac{1}{N} \times \sum_{n=0}^{N-1} V'_{insp,corr}(n) - V'_{gas\ sample} - V'_{bias,e} - V'_{compl} \quad (39)$$

where $V'_{insp,corr}(0)$ and $V'_{insp,corr}(N-1)$ are the first and last inspiratory flow samples, respectively, in the consecutive respiratory cycles. This determination (at ATP) assumes no use of humidifier in the inspiratory limb but can be modified to account for humidification.

The system can calculate the water vapor pressure in the inspired gas:

$$P_{H2O,insp} = P_{H2O,sat}(t_{amb}) \times RH(t_{amb}), \quad (40)$$

where $P_{H2O,sat}$ is a function of temperature.

In addition, the system estimates the expired minute ventilation V'$_E$ (at BTPS) by use of (initial) V'O$_2$ and RQ value (settings):

$$V'_E = V'_I \times \frac{310}{273 + t_{amb}} \times \frac{P_B - P_{H2O,insp}}{P_B - 47} - V'O_2 \times (1 - RQ) \times \frac{310}{273} \times \frac{P_B}{P_B - 47} \quad (41)$$

The system can also calculate the total inspiratory ventilation (at ATP), i.e., the total flow which flushes the whole length of the inspiratory limb:

$$V'_{I,tot} = V'_I + V'_{compl} + V'_{bias,e} \quad (42)$$

In the next step, the system calculates the total expiratory ventilation (mixture of ATP and BTPS amounts), i.e., the total flow which flushes the whole length of the expiratory limb, assuming no change in temperature of expired gas from Y-piece to mixing chamber:

$$V'_{E,tot} = V'_E + V'_{compl} + V'_{bias,e} \quad (43)$$

The system can also calculate the I-E delay time:

$$T_{I-E\,delay} = \left(\frac{V_{DS,I-Y}}{V'_{I,tot}} + \frac{(V_{DS,E} + V_{DS,V} + V_{DS,M})}{V'_{E,tot}}\right) \times 60 \text{ s/min} \quad (44)$$

In addition, the system can calculate the number of whole breaths corresponding to the I-E delay time:

$$N_{I-E\,delay} = \left[\frac{T_{I-E\,delay}}{60 \text{ s/min}} \times RR\right] \quad (45)$$

The system can also calculate the number of breaths to skip to allow flushing of the gas sample inlets after switching inlet between inspiration and expiration:

$$N_{skip} = \left[\frac{T_{FDG,I} + T_{flush}}{60 \text{ s/min}} \times RR\right] + 1 \quad (46)$$

The system can also calculate the number of samples corresponding to the lengths of the gas sample tubing:

$$N_{FGD,I} = \left[\frac{T_{FGD,I}}{\Delta t}\right] \quad (47)$$

$$N_{FGD,E} = \left[\frac{T_{FGD,E}}{\Delta t}\right] \quad (48)$$

Gas calibrations as well as subsequent measurements are performed using the Nafion® sample tubes for accurate gas analysis. As the tubes work for both drying and humidifying gas streams they also humidify dry calibration gases, which allows calibration at humidity levels equal to those seen during measurements. Since calibration set points are given for dry gas, subsequent measurements will also provide fractional concentrations of dry gas no matter if the gas is dry (inspiration) or wet (expiration).

The flowmeter 120 is calibrated on e.g. air at ATP using a syringe (e.g., 1 L). The offset is calibrated automatically prior to a measurement (and regularly during long-term measurements) by connecting both differential pressure sensor ports to the same pressure tube or ambient air using one or two solenoid valves. The flow-gas delay is factory calibrated and only needs re-calibration in case the sample flow or length of inspiratory gas sample tubing is changed.

Figure 6A:
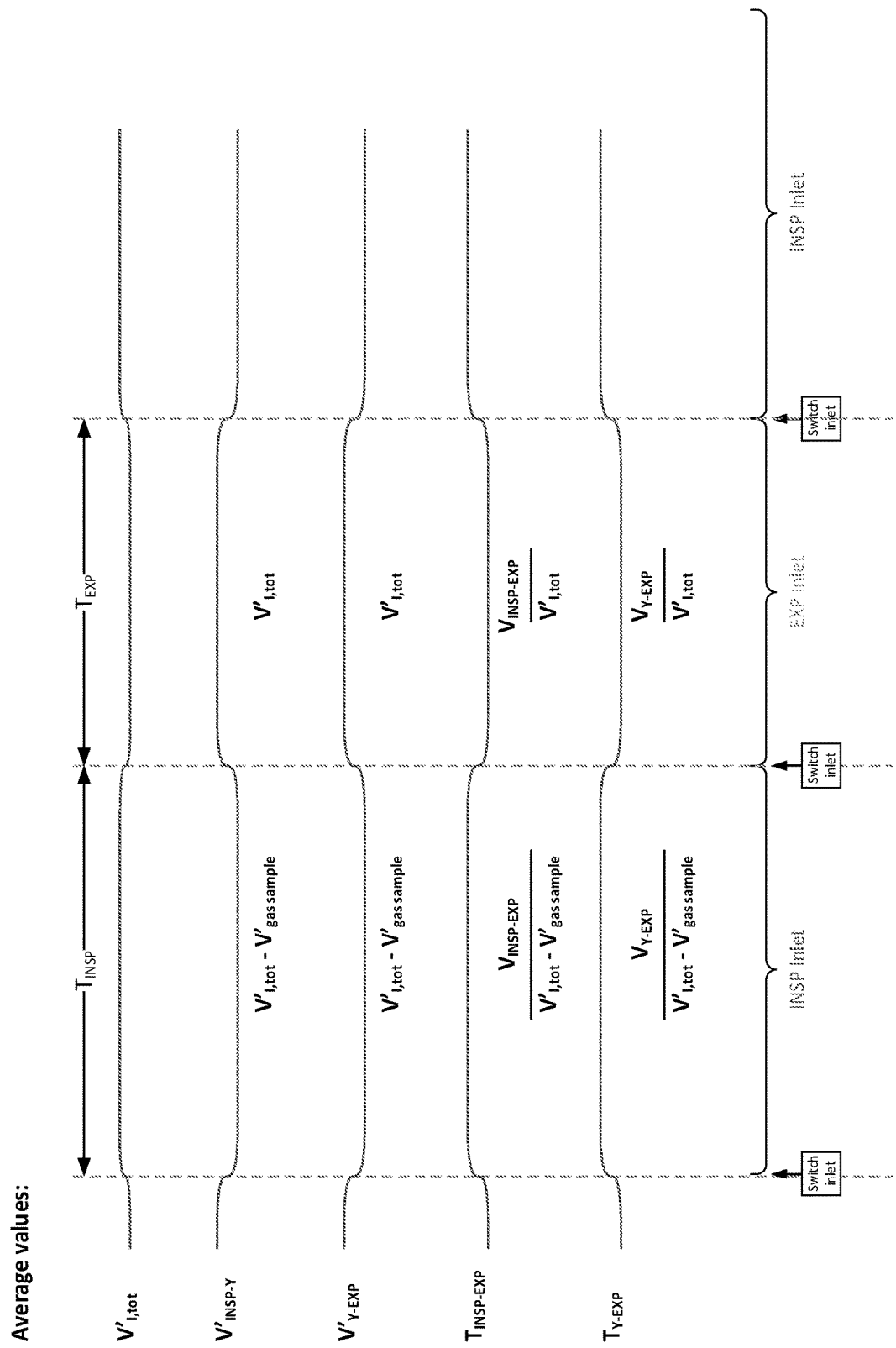
FIGS. 6A and 6B are exemplary inspiratory and expiratory signal diagrams using the system for determining flows and time periods as depicted with respect to FIG. 5.
Figure 6B:
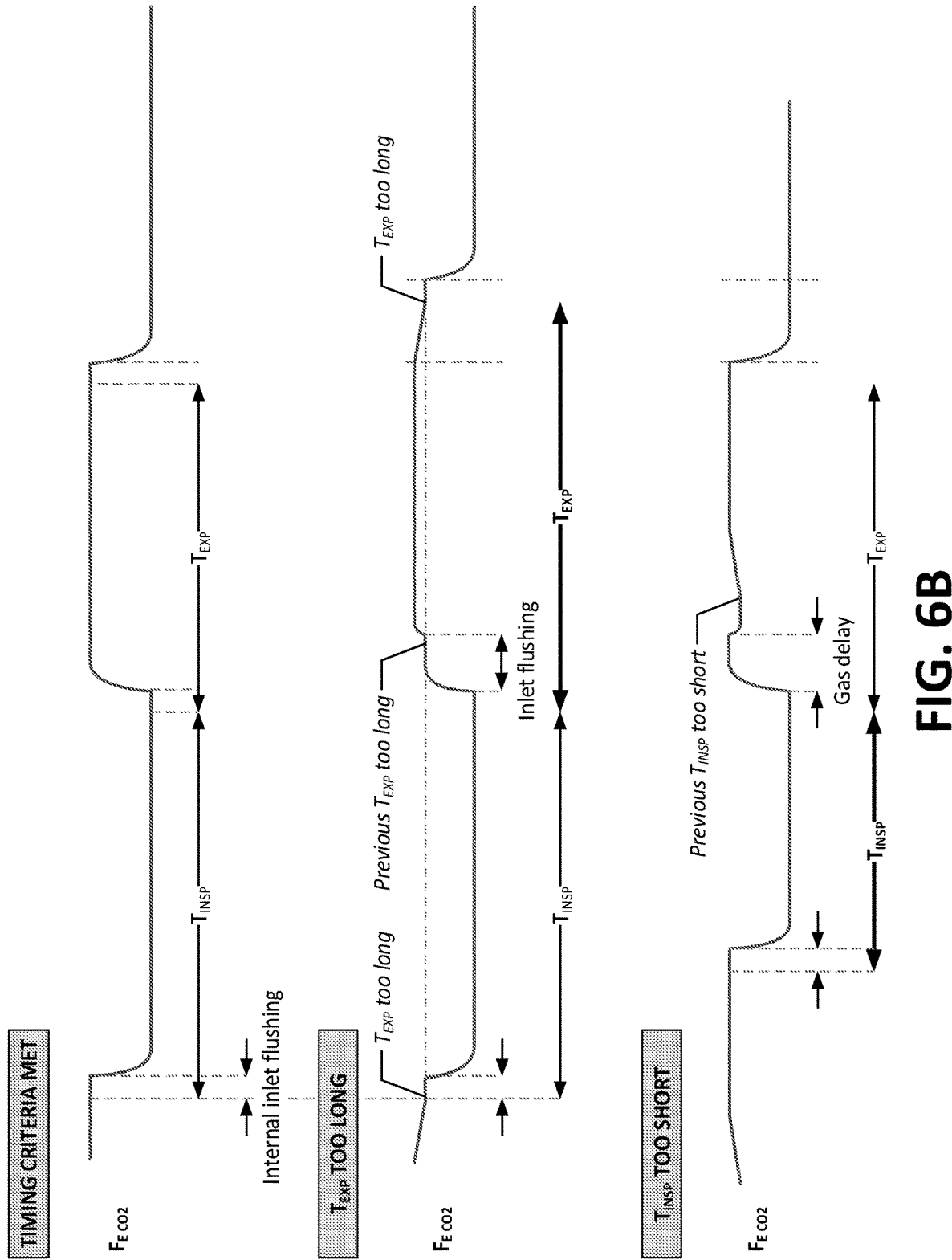

FIGS. 6A and 6B are exemplary inspiratory and expiratory signal diagrams using the system for determining flows and time periods. FIG. 6A shows qualitatively, and assuming steady-state conditions, how flow rates and transport delay times vary depending on which sampling inlet is active (i.e. sampling gas). The change in the upper curve, V'$_{I,tot}$, is caused by the fact that the ventilator is assumed to compensate for the gas consumed by the inspiratory inlet during the INSP sampling period when using pressure controlled ventilation mode. FIG. 6B illustrates qualitatively, using CO$_2$ as example and assuming steady-state conditions, how mixed expired gas concentration measured at the expiratory sampling point changes depending on the timing sequence. The upper panel shows a steady F$_E$CO$_2$ level obtained with an optimal timing sequence. The panel in the middle shows how the F$_E$CO$_2$ level decays if the expiratory sampling period is too long. The change in F$_E$CO$_2$ level is more clearly detected in the beginning of the expiratory sampling period at the transition when the expiratory sampling inlet (containing gas from the previous expiratory sampling period) has been flushed. Likewise, the lower panel shows what could happen if the previous inspiratory sampling period was too short. In this case, the initial F$_E$CO$_2$ level reflects the "correct" concentration from the end of the previous period, however, after flushing of the expiratory sampling inlet there will be an intermediate period with a decrease in F$_E$CO$_2$ level caused by the increased dilution of expiratory gas with inspiratory gas when sampling from the expiratory sampling inlet, combined with the fact that the "correct" concentration has not yet reached the expiratory sampling point because of a too short inspiratory sampling period.

Figure 7:
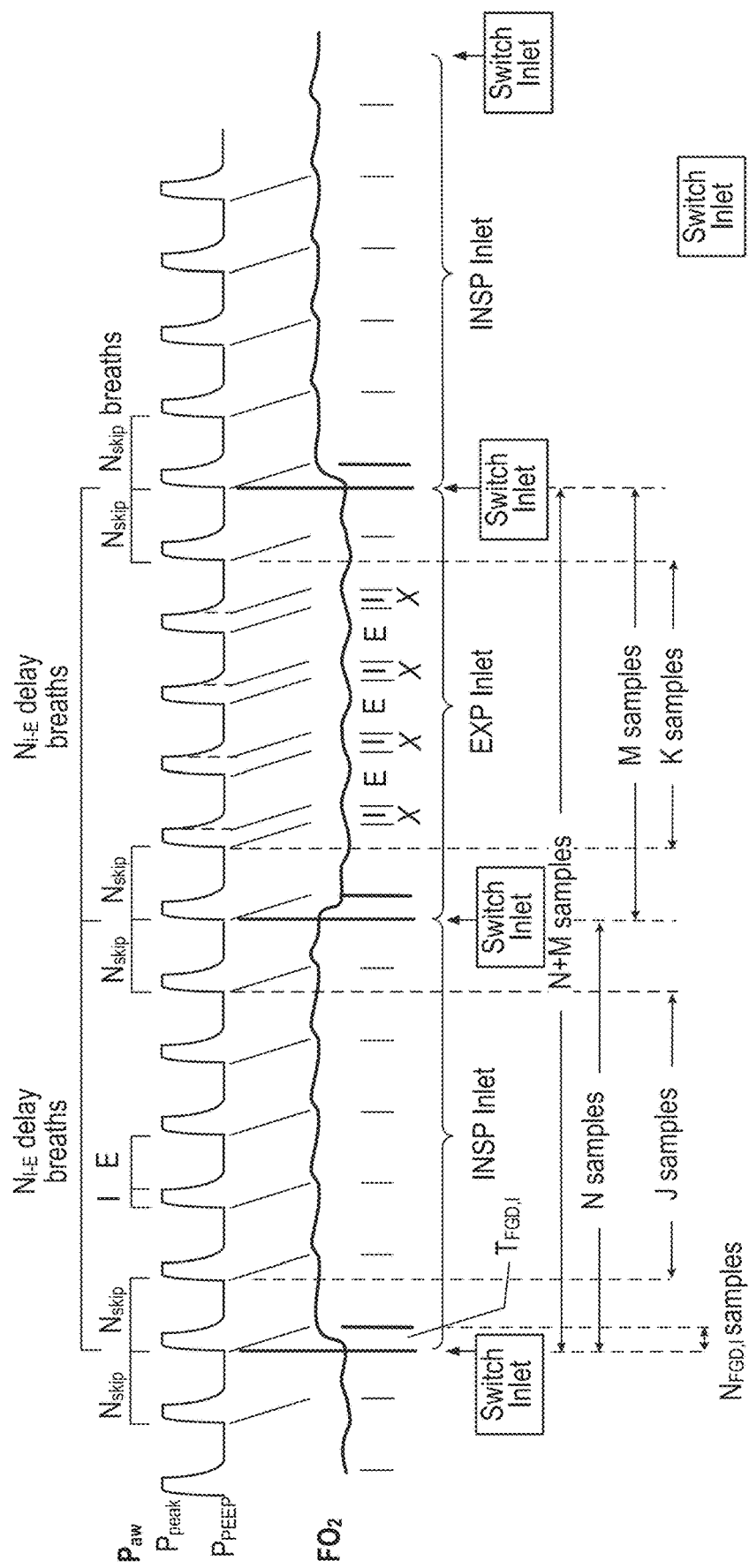
FIG. 7 is a graphical representation of the timing sequence for calculations for each inspiratory and expiratory gas sample measurement cycle.

FIG. 7 shows the timing sequence for calculations for each inspiratory and expiratory gas sample measurement cycle, respectively. Using O$_2$ as example, and assuming steady-state and optimal timing, the figure shows how the measured gas concentration changes between inspiratory and expiratory sampling periods.

EXAMPLES

The invention is further described in the following examples, which do not limit the scope of the invention described in the claims.

Example 1—In Vitro Lung Simulator Experiments

Figure 8:
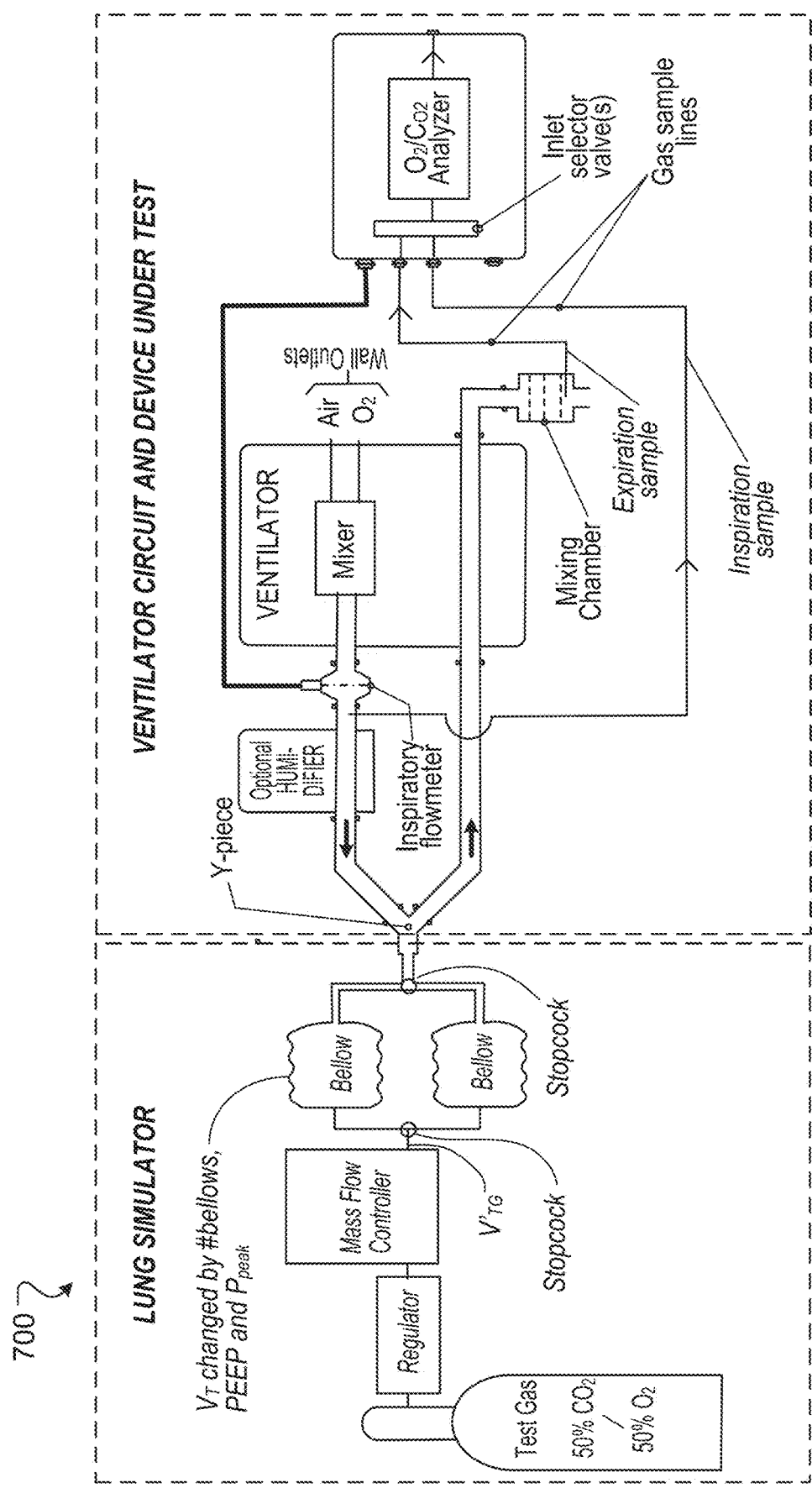
FIG. 8 is a schematic of a lung simulator that permits the quantification of oxygen consumption and carbon dioxide production during phasic ventilation of the apparatus described herein.

FIG. 8 shows the setup for using a lung simulator 700 to quantify oxygen consumption and carbon dioxide production during phasic ventilation. Gold standard measures of each are provided by an inflow of precise volumes of oxygen and carbon dioxide using a mass flow controller.

The lung simulator 700 had artificial lungs in which V'O$_2$ and V'CO$_2$ are simulated with precision using a mass flow controller. This in vitro system had a silicone bellows reservoir including a minimum volume (i.e. FRC) and a tidal volume. To simulate metabolic gas exchange, a flow of a precision test gas with known fractional concentrations of CO$_2$ and O$_2$ (50% CO$_2$, balance O$_2$ with 0.03% absolute accuracy) was continuously infused at a constant rate (0-50 mL/min using a mass flow controller with an accuracy of ±0.6% at full-scale). It should be noted that the lung simulator produces negative V'O$_2$ (i.e., O$_2$ production). The system permitted a standard ventilator to drive phasic respiration, to apply bias flow, to titrate F$_I$O$_2$, and to permit simultaneous humidification.

The performance of the novel device among a range of V'O$_2$, RR and F$_I$O$_2$ values are shown in Table 1. Note that in all cases the error was <1 mL/min of V'O$_2$ (most were <0.5 mL/min), even when interrogated at RR as high as 80 breaths/minute, V$_T$ as low as 10 mL, and F$_I$O$_2$ as high as 60%. These findings cover the clinically relevant range in infants and neonates, and provide significant optimism that this system will be able to accurately measure V'O$_2$. V'CO$_2$ is measured by this system with even greater accuracy (since F$_I$CO$_2$ is always negligible).

TABLE 1

| Ventilator settings | | | VO2 | | Error |
|---|---|---|---|---|---|
| FIO2 % | VT mL | RR BPM | Set mL/min* | Meas. mL/min* | Abs. mL/min* |
| 21 | 15 | 30 | 10 | 9.98 | −0.02 |
| 21 | 10 | 30 | 5 | 4.90 | −0.10 |
| 40 | 15 | 30 | 10 | 9.38 | −0.62 |
| 40 | 10 | 30 | 5 | 4.72 | −0.28 |
| 60 | 15 | 30 | 10 | 9.50 | −0.50 |
| 60 | 10 | 30 | 5 | 5.10 | 0.10 |
| 40 | 10 | 20 | 5 | 4.62 | −0.38 |
| 40 | 10 | 45 | 5 | 4.99 | −0.01 |
| 40 | 10 | 60 | 5 | 4.73 | −0.27 |
| 40 | 10 | 80 | 5 | 5.33 | 0.33 |

Example 2—In Vivo Rat Experiments

Referring to FIG. 8, to simulate the performance of the device in extremely low birth weight infants, we compared measures of V'O$_2$ and V'CO$_2$ in Sprague Dawley (N=5, weight 662±61 g). Animals were intubated and the trachea sealed against the ETT using suture purse string. They were ventilated using a Servo-i ventilator in pressure control, bias flow of 0.5 L/min, PEEP of 5 cmH$_2$O, peak pressure 20 cmH$_2$O and mandatory rate of 30 bpm. F$_I$O$_2$ was maintained at 0.4. In each experiment, V'O$_2$ measurements were made under two conditions: 40% F$_I$O$_2$ provided by the ventilator as in clinical practice, and when provided using a certified gas mixture of 40% F$_I$O$_2$ with <+0.03% absolute accuracy. The latter condition was used to obviate the complicating factor of fluctuations in F$_I$O$_2$ as described above. In both conditions, device measurements were compared to those calculated using a Douglas bag method.

Expired gases were collected within a 5 L non-diffusing gas collection bag connected to the exhaust port of the ventilator. The bag was flushed three times with expired gas and emptied. Then, measurements were performed with the device and gas collected simultaneously for comparison over ~6 minutes. The contents of the bag were subsequently analyzed, its volume measured with a calibrated syringe, and V'O$_2$ and V'CO$_2$ calculated using the Douglas technique. As shown in Table 2, differences between device estimates and reference measurements were below 0.4 mL/min in all cases, which would be clinically acceptable for even the smallest infants. During the completion of these experiments, we did not note any significant technical problems with the ventilator and its interaction with the ventilation of the animal.

TABLE 2

| Insp. source | Mixing technique | | Douglas bag | | Difference | |
|---|---|---|---|---|---|---|
| | VO$_2$ mL/min | VCO$_2$ mL/min | VO$_2$ mL/min | VCO$_2$ mL/min | VO$_2$ mL/min | VCO$_2$ mL/min |
| Avg. | 7.84 | 6.46 | 8.17 | 6.24 | −0.34 | 0.23 |
| Vent. | 8.00 | 6.71 | 8.35 | 6.51 | −0.35 | 0.20 |
| Tank | 7.67 | 6.22 | 8.00 | 5.97 | −0.33 | 0.25 |

N = 5 (625-770 g)

OTHER EMBODIMENTS

It is to be understood that while the invention has been described in conjunction with the detailed description thereof, the foregoing description is intended to illustrate and not limit the scope of the invention, which is defined by the scope of the appended claims. For example, the principle discussed herein also works in circuits where a bias flow is being applied. The bias flow leads to higher inspiratory flow rates but correspondingly lower I-E differences in O$_2$ and CO$_2$ concentrations and therefore equal metabolic rates. However, such a system is more prone to gas measurement errors in case a bias flow is applied for flow triggering by the ventilator.

Other aspects, advantages, and modifications are within the scope of the following claims.

What is claimed is:

1. A computing device-implemented method to determine oxygen consumption in a mechanically ventilated patient, the method comprising:
   receiving a signal representing a total flow at an inspiratory outlet of a ventilator;
   calculating a transport delay time between inspiratory and expiratory gas sample points in a patient ventilation circuitry;
   transmitting a signal to an inlet selector valve to selectively open a fluid path between the inspiratory gas sample point and an oxygen sensor or between the expiratory gas sample point and the oxygen sensor, wherein
      the inspiratory gas sample point is located in the fluid path of the patient ventilation system between the patient and a source of air and oxygen, and
      the expiratory gas sample point is located in the fluid path of the patient ventilation system between the patient and a fluid outlet or a mixing chamber fluidly connected to the fluid outlet;
   receiving data representing oxygen content and carbon dioxide content over a period of time;
   calculating oxygen consumption data over the period of time from the data representing the total flow, oxygen content and carbon dioxide content and from the transport delay time; and
   displaying the oxygen consumption data over the period of time.

2. The method of claim 1, further comprising repeating the transmitting and receiving steps over an observation period longer than the period of time.

3. The method of claim 1, wherein calculating oxygen consumption comprises calculating a number of whole breaths of a patient from the delay time.

4. The method of claim 1, further comprising correcting the signal representing the total flow for viscosity dependence.

5. The method of claim 1, further comprising calculating flow-weighted averages of the inspiratory oxygen content and carbon dioxide content.

6. The method of claim 1, further comprising calculating a respiratory quotient of a patient.

7. The method of claim 1, further comprising calculating carbon dioxide production of a patient.

8. The method of claim 1, further comprising calculating energy expenditure of a patient.

9. The method of claim 1, further comprising calculating a transport delay time between a Y-connector that is attachable to a patient and the expiratory gas sample point.

10. The method of claim 1, wherein the patient is a neonate.

11. A computing device-implemented method of claim 1, further comprising:
correcting the signal representing the flow for viscosity dependence;
calculating a further transport delay time between a Y-connector that is attachable to a patient and the expiratory gas sample point; and
calculating flow-weighted averages of the oxygen content and carbon dioxide content.

12. A patient ventilation system comprising:
a ventilation fluid circuit with a fluid path connected to sources of air and oxygen, a fluid outlet, and a Y-connector that is attachable to a patient;
a flowmeter located in the fluid path between the sources of air and oxygen and the Y-connector;
an inhalation fluid sampling line connected at an inhalation gas sample point of the fluid path located between the sources of air and oxygen and the Y-connector;
an exhalation fluid sampling line connected to an exhalation gas sample point of the fluid path located between the patient and the fluid outlet or a mixing chamber fluidly connected to the fluid outlet;
an oxygen sensor and a carbon dioxide sensor configured to measure an oxygen concentration and a carbon dioxide concentration of a gas passing along a sensing path through the sensor, wherein the sensing path is connected to the inhalation fluid sampling line and to the exhalation fluid sampling line;
a selector valve arranged to selectively connect either the inhalation fluid sampling line or the exhalation fluid sampling line to the sensing path; and
a computing device comprising a memory configured to store instructions and a processor to execute the instructions to perform operations comprising:
receiving a signal representing a total flow at an inspiratory outlet of a ventilator;
calculating a transport delay time between inhalation and exhalation gas sample points;
transmitting a signal to the selector valve to selectively connect either the inhalation fluid sampling line or the exhalation fluid sampling line to the sensing path;
receiving data representing oxygen content and carbon dioxide content over a period of time;
calculating oxygen consumption data over the period of time from the data representing the total flow, oxygen content and carbon dioxide content, and from the transport delay time; and
displaying the oxygen consumption data.

13. The system of claim 12, wherein the inhalation fluid sampling line, the exhalation fluid sampling line, or both the inhalation fluid sampling line and the exhalation fluid sampling line, are water permeable gas tubes that equilibrate their contents to ambient humidity.

14. The system of claim 13, wherein the computing device performs a further operation comprising calculating carbon dioxide production.

15. The system of claim 13, wherein the computing device performs a further operation comprising calculating an energy expenditure of the patient.

16. The system of claim 12, wherein a portion of the ventilation fluid circuit is inside a ventilator.

17. The system of claim 12, wherein the computing device performs a further operation comprising calculating a respiratory quotient of the patient.

18. The system of claim 12, wherein the oxygen sensor comprises a laser diode sensor and the carbon dioxide sensor is a nondispersive infra-red sensor.

19. A patient ventilation system comprising:
a ventilation fluid circuit with a fluid path connected to sources of air and oxygen, a fluid outlet, and a Y-connector that is attachable to a patient;
an inhalation fluid sampling line connected at an inhalation gas sample point of the fluid path located between the sources of air and oxygen and the Y-connector;
an exhalation fluid sampling line connected to an exhalation gas sample point of the fluid path located between the Y-connector and the fluid outlet or a mixing chamber fluidly connected to the fluid outlet;
an oxygen sensor and a carbon dioxide sensor configured to measure an oxygen concentration and a carbon dioxide concentration of a gas passing along a sensing path through the sensor, wherein the sensing path is connected to the inhalation fluid sampling line and to the exhalation fluid sampling line;
a selector valve arranged to selectively connect either the inhalation fluid sampling line or the exhalation fluid sampling line to the sensing path; and
a computing device comprising a memory configured to store instructions and a processor to execute the instructions to perform operations comprising:
receiving a signal representing a total flow at an inspiratory outlet of a ventilator;
correcting the signal representing the total flow for viscosity dependence;
calculating a transport delay time between inspiratory and expiratory gas sample points in the ventilation fluid circuit;
transmitting a signal to an inlet selector valve to selectively open a fluid path between the inspiratory gas sample point and an oxygen sensor or between the expiratory gas sample point and the oxygen sensor;
receiving data representing oxygen content and carbon dioxide content over a period of time;
calculating flow-weighted averages of the oxygen content and carbon dioxide content;
calculating oxygen consumption data over the period of time from the data representing oxygen content and carbon dioxide content and from the transport delay time; and
displaying the oxygen consumption data over the period of time.

* * * * *